(12) United States Patent
Snutch et al.

(10) Patent No.: US 7,666,865 B2
(45) Date of Patent: *Feb. 23, 2010

(54) CALCIUM CHANNEL BLOCKERS

(75) Inventors: Terrance P. Snutch, Vancouver (CA); Gerald W. Zamponi, Calgary (CA)

(73) Assignee: Neuromed Pharmaceuticals Ltd., Vancouver (CA)

(*) Notice: Subject to any disclaimer, the term of this patent is extended or adjusted under 35 U.S.C. 154(b) by 551 days.

This patent is subject to a terminal disclaimer.

(21) Appl. No.: 11/601,005

(22) Filed: Nov. 16, 2006

(65) Prior Publication Data

US 2007/0185105 A1  Aug. 9, 2007

Related U.S. Application Data

(63) Continuation of application No. 10/655,393, filed on Sep. 3, 2003, now Pat. No. 7,186,726, which is a continuation-in-part of application No. 10/060,900, filed on Jan. 29, 2002, now Pat. No. 6,617,322, which is a continuation of application No. 09/476,927, filed on Dec. 30, 1999, now Pat. No. 6,387,897, which is a continuation-in-part of application No. 09/401,699, filed on Sep. 23, 1999, now Pat. No. 6,294,533, which is a continuation-in-part of application No. 09/107,037, filed on Jun. 30, 1998, now Pat. No. 6,011,035.

(51) Int. Cl.
*A61K 31/535* (2006.01)
*A61K 31/4965* (2006.01)
*A61K 31/445* (2006.01)
*A61K 31/41* (2006.01)
*C07D 295/00* (2006.01)

(52) U.S. Cl. .............. 514/231.2; 514/255.01; 514/315; 514/381; 514/391; 544/106; 544/381; 544/391

(58) Field of Classification Search .............. 514/231.2, 514/255.01, 315, 381, 391; 544/106, 381, 544/391
See application file for complete search history.

(56) References Cited

U.S. PATENT DOCUMENTS

| | | | |
|---|---|---|---|
| 3,288,795 A | 11/1966 | Irikura et al. | |
| 4,188,485 A | 2/1980 | Kukla | |
| 4,918,073 A | 4/1990 | Ruger et al. | |
| 5,386,025 A | 1/1995 | Jay et al. | |
| 5,428,038 A | 6/1995 | Chatterjee et al. | |
| 5,623,051 A | 4/1997 | Catterall et al. | |
| 5,646,149 A | 7/1997 | Hellberg et al. | |
| 5,703,071 A | 12/1997 | Itoh et al. | |
| 6,011,035 A | 1/2000 | Snutch et al. | |
| 6,294,533 B1 * | 9/2001 | Snutch et al. | 514/231.2 |
| 6,387,897 B1 * | 5/2002 | Snutch | 514/231.2 |
| 6,617,322 B2 * | 9/2003 | Snutch | 514/231.2 |
| 7,186,726 B2 * | 3/2007 | Snutch et al. | 514/255.01 |

FOREIGN PATENT DOCUMENTS

| | | |
|---|---|---|
| EP | 0187524 | 7/1986 |
| EP | 0458387 | 11/1991 |
| ES | 504202 | 1/1983 |
| ES | 514167 | 4/1983 |
| GB | 1513883 | 6/1978 |
| WO | WO-99/15129 | 4/1999 |
| WO | WO-99/25686 | 5/1999 |

OTHER PUBLICATIONS

Galizzi, J-P. et al. *Proc Natl Acad Sci USA* (1986) 83:7513-7517.
Gould, R.J. et al. *Proc Natl Acad Sci USA* (1983) 80:5122-5125.
Grantham, C.J. et al. *Brit J Pharmacol* (1994) 111:438-488.

(Continued)

*Primary Examiner*—Raymond J Henley, III
(74) *Attorney, Agent, or Firm*—Morrison & Foerster LLP

(57) ABSTRACT

Compounds of the formula

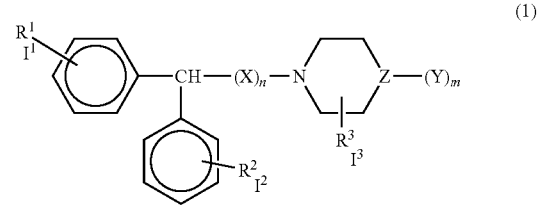

(1)

wherein m is 0, 1 or 2;
wherein when m is 0, Z is O, when m is 1, Z is N, and when m is 2, Z is C;
Y is H, OH, $NH_2$, or an organic moiety of 1-20C, optionally additionally containing 1-8 heteroatoms selected from the group consisting of N, P, O, S and halo;
each $l^1$ and $l^2$ is independently 0-5;
$l^3$ is 0 or 1;
each of $R^1$, $R^2$ and $R^3$ is independently alkyl (1-6C), aryl (6-10C) or arylalkyl (7-16C) optionally containing 1-4 heteroatoms selected from the group consisting of halo, N, P, O, and S or each of $R^1$ and $R^2$ may independently be halo, COOR, $CONR_2$, $CF_3$, CN or $NO_2$, wherein R is H or lower alkyl (1-4C) or alkyl (1-6C);
n is 0 or 1;
X is a linker;
with the proviso that Y is not a tropolone, a coumarin, or an antioxidant containing an aromatic group and with the further proviso that if $l^3$ is 0, and either $l^1$ and $l^2$ is 0 or 1 and if $R^1$ and/or $R^2$ represent F in the para position, Z cannot be C or N; and
are useful to treat pain. Libraries of these compounds can also be used to identify antagonists for other targets.

2 Claims, 4 Drawing Sheets

OTHER PUBLICATIONS

Ito, C. et al. *Eur J Pharmacol* (1994) 257:203-210.
King, V.F. et al. *J Biol Chem* (1989) 264:5633-5641.
"Lomerizine Kanebo KK" published in *Current Opinion in CPNS Investigational Drugs* (1999) 1(1):116-125.
Bourinet et al., Nature Neuroscience (1999) 2:407-415.
Cohan et al., Annals of the New York Academy of Sciences (1991) 635:397-399.
Cribbs et al., Circulation Research (1998) 83:103-109.
Database WPI Week 9711, Derwent Publications Ltd. London, GB; Abstract JP09 003067, XP002133055 (Hisamitsu Pharm Co Ltd.) Jan. 7, 1997.
De Waard et al., Ion Channels (Narahashi, ed., Plenum Press, NY, 1997) 4:41-87.
Dhainaut et al., J Med Chem (1992) 35:2481-2496.
Dooley, Current Opinion in CPNS Investigational Drugs (1999) 1(1):116-125.
Dunlap et al., Trends Neurosci (1995) 18:89-98.
Estep et al., J Med Chem (1995) 38:2582-2595.
Galizzi et al., PNAS USA (1986) 83:7513-7517.
Glamkowski et al., J Med Chem (1977) 20(11):1485-1489.
Gould et al., PNAS (1983) 80:5122-5125.
Grantham et al., Brit J Pharmacol (1994) 111:438-488.
Ito et al., Eur J Pharmacol (1994) 257:203-210.
King et al., J Biol Chem (1989) 264:5633-5641.
Lee et al., Journal of Neuroscience (1999) 19:1912-1921.
Lehmann et al., Arch Pharm (1988) 321:807-812.
McCleskey et al., Curr Topics Membr (1991) 39:295-326.
Miyano et al., Chem Pharm Bull (1990) 38(6):1570-1574.
Ohtaka et al., Chem Pharm Bull (1987) 35(8):3270-3275.
Ohtaka et al., Chem Pharm Bull (1987) 35(10):4117-4123.
Perez-Reyes et al., Nature (1998) 391:896-900.
Prasad et al., J Med Chem (1968) 11(6):1144-1150.
Sather et al., Neuron (1993) 11:291-303.
Stea et al., Handbook of Receptors and Channels (North, ed., CRC Press 1995) 113-151.
Stea et al., PNAS USA (1994) 91:10576-10580.
Tytgat et al., Brain Research (1991) 549:112-117.
Uneyama et al., Calcium Ion Modulator, Sel Pap Satell Symp (1988) 13-23.
Vadodaria et al., J Med Chem (1969) 12:860-865.
Zikolova et al., Tr Nauchnoizsled Khim—Farm Inst (1984) 14:23-28.
Zikolova et al., Tr Nauchnoizsled Khim—Farm Inst (1972) 8:59-67.

\* cited by examiner

Penfluridol:

Pimozide:

Haloperidol:

Flunarizine:

compounds lacking blocking activity at 10 μM concentrations

Tolylpiperazine – HCl:

Trifluoromethylphenothiazine:

Morpholineacetophenone:

Morpholinebenzophenone:

Procaine:

compounds lacking blocking activity at 10 μM concentrations

Piperine:

Fornocaine:

Flecainide:

Prenylamine:

$\alpha_{1B}$N-type: IC50 > 40 μM compounds lacking blocking activity at 10 μM concentrations

Pridinol:

$\alpha_{1B}$ N-type: IC$_{50}$ > 400 μM

Primidone:

$\alpha_{1B}$ N-type: IC$_{50}$ > 500 μM

Piperidolate:

$\alpha_{1B}$ N-type: IC$_{50}$ > 300 μM

US 7,666,865 B2

CALCIUM CHANNEL BLOCKERS

Cross-Reference to Related Applications

This application is a continuation of U.S. Ser. No. 10/655,393 filed 3 Sep. 2003 and now U.S. Pat. No. 7,186,726 which is a continuation-in-part of U.S. Ser. No. 10/060,900 filed 29 Jan. 2002, now U.S. Pat. No. 6,617,322; which is a continuation of U.S. Ser. No. 09/476,927 filed 30 Dec. 1999 and now U.S. Pat. No. 6,387,897 which is a continuation-in-part of U.S. Ser. No. 09/401,699 filed 23 Sep. 1999 and now U.S. Pat. No. 6,294,533 which is a continuation-in-part of U.S. Ser. No. 09/107,037 filed 30 Jun. 1998 and now U.S. Pat. No. 6,011,035. The contents of these documents are incorporated herein by reference.

TECHNICAL FIELD

The invention relates to compounds useful in treating conditions associated with calcium channel function. More specifically, the invention concerns compounds containing benzhydril and 6-membered heterocyclic moieties that are useful in treatment of conditions such as stroke and pain.

BACKGROUND ART

Native calcium channels have been classified by their electrophysiological and pharmacological properties as T, L, N, P and Q types (for reviews see McCleskey, E. W., et al., *Curr Topics Membr* (1991) 39:295-326, and Dunlap, K., et al., *Trends Neurosci* (1995) 18:89-98). T-type (or low voltage-activated) channels describe a broad class of molecules that transiently activate at negative potentials and are highly sensitive to changes in resting potential. The L, N, P and Q-type channels activate at more positive potentials and display diverse kinetics and voltage-dependent properties. There is some overlap in biophysical properties of the high voltage-activated channels, consequently pharmacological profiles are useful to further distinguish them. L-type channels are sensitive to dihydropyridine agonists and antagonists, N-type channels are blocked by the *Conus geographus* peptide toxin, ω-conotoxin GVIA, and P-type channels are blocked by the peptide ω-agatoxin IVA from the venom of the funnel web spider, *Agelenopsis aperta*. A fourth type of high voltage-activated calcium channel (Q-type) has been described, although whether the Q- and P-type channels are distinct molecular entities is controversial (Sather, W. A., et al., *Neuron* (1995) 11:291-303; Stea, A., et al., *Proc Natl Acad Sci USA* (1994) 91:10576-10580). Several types of calcium conductances do not fall neatly into any of the above categories and there is variability of properties even within a category suggesting that additional calcium channels subtypes remain to be classified.

Biochemical analyses show that neuronal high voltage activated calcium channels are heterooligomeric complexes consisting of three distinct subunits ($\alpha_1$, $\alpha_2\delta$ and $\beta$) (reviewed by De Waard, M., et al., *Ion Channels* (1997) vol. 4, Narahashi, T. ed. Plenum Press, NY). The $\alpha_1$ subunit is the major pore-forming subunit and contains the voltage sensor and binding sites for calcium channel antagonists. The mainly extracellular $\alpha_2$ is disulfide-linked to the transmembrane $\delta$ subunit and both are derived from the same gene and are proteolytically cleaved in vivo. The $\beta$ subunit is a nonglycosylated, hydrophilic protein with a high affinity of binding to a cytoplasmic region of the $\alpha_1$ subunit. A fourth subunit, $\gamma$, is unique to L-type calcium channels expressed in skeletal muscle T-tubules. The isolation and characterization of γ-subunit-encoding cDNAs is described in U.S. Pat. No. 5,386,025 which is incorporated herein by reference.

Recently, each of these $\alpha_1$ subtypes has been cloned and expressed, thus permitting more extensive pharmacological studies. These channels have been designated $\alpha_{1A}$-$\alpha_{1E}$, $\alpha_{1G}$ and $\alpha_{1S}$ and correlated with the subtypes set forth above. $\alpha_{1A}$ channels are of the P/Q type; $\alpha_{1B}$ represents N; $\alpha_{1C}$, $\alpha_{1D}$ and $\alpha_{1S}$ represent L; $\alpha_{1E}$ represents a novel type of calcium conductance, and $\alpha_{1G}$ represents one member of the T-type family, reviewed in Stea, A., et al., in *Handbook of Receptors and Channels* (1994), North, R. A. ed., CRC Press; Perez-Reyes, et al., *Nature* (1998) 391:896-900.

U.S. Pat. No. 5,646,149 describes calcium antagonists of the formula A-Y-B wherein B contains a piperazine or piperidine ring directly linked to Y. An essential component of these molecules is represented by A, which must be an antioxidant; the piperazine or piperidine itself is said to be important. The exemplified compounds contain a benzhydril substituent, based on known calcium channel blockers (see below). U.S. Pat. No. 5,703,071 discloses compounds said to be useful in treating ischemic diseases. A mandatory portion of the molecule is a tropolone residue; among the substituents permitted are piperazine derivatives, including their benzhydril derivatives. U.S. Pat. No. 5,428,038 discloses compounds which are said to exert a neural protective and antiallergic effect. These compounds are coumarin derivatives which may include derivatives of piperazine and other six-membered heterocycles. A permitted substituent on the heterocycle is diphenylhydroxymethyl. Thus, approaches in the art for various indications which may involve calcium channel blocking activity have employed compounds which incidentally contain piperidine or piperazine moieties substituted with benzhydril but mandate additional substituents to maintain functionality.

Certain compounds containing both benzhydril moieties and piperidine or piperazine are known to be calcium channel antagonists and neuroleptic drugs. For example, Gould, R. J., et al., *Proc Natl Acad Sci USA* (1983) 80:5122-5125 describes antischizophrenic neuroleptic drugs such as lidoflazine, fluspirilene, pimozide, clopimozide, and penfluridol. It has also been that fluspirilene binds to sites on L-type calcium channels (King, V. K., et al., *J Biol Chem* (1989) 264:5633-5641) as well as blocking N-type calcium current (Grantham, C. J., et al., *Brit J Pharmacol* (1944) 111:483-488).

The present invention is based on the recognition that the combination of a six-membered heterocyclic ring containing at least one nitrogen coupled optionally through a linker to a benzhydril moiety not only results in calcium channel blocking activity, but also enhanced specificity for N-type channels, thus making these compounds particularly useful for treating stroke and pain. By focusing on these moieties, compounds useful in treating indications associated with excessive calcium channel activity and combinatorial libraries that contain these compounds can be prepared.

DISCLOSURE OF THE INVENTION

The invention relates to compounds useful in treating conditions such as stroke, chronic and acute pain, epilepsy, hypertension, cardiac arrhythmias, and other indications associated with calcium metabolism. The compounds of the invention are benzhydril derivatives of piperidine, piperazine, or morpholine with substituents which enhance the calcium channel blocking activity of the compounds but do not contain substituents that are antioxidants, tropolones or coumarins. Thus, in one aspect, the invention is directed to therapeutic methods that employ compounds of the formula

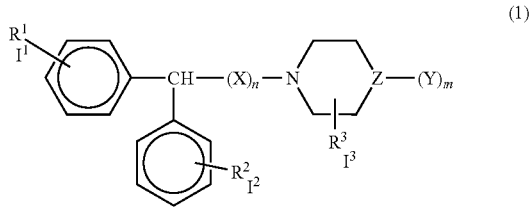

(1)

wherein m is 0, 1 or 2;

wherein when m is 0, Z is O, when m is 1, Z is N, and when m is 2, Z is C;

Y is H, OH, $NH_2$, or an organic moiety of 1-20C, optionally additionally containing 1-8 heteroatoms selected from the group consisting of N, P, O, S and halo;

each $l^1$ and $l^2$ is independently 0-5;

$l^3$ is 0 or 1;

each of $R^1$, $R^2$ and $R^3$ is independently alkyl (1-6C), aryl (6-10C) or arylalkyl (7-16C) optionally containing 1-4 heteroatoms selected from the group consisting of halo, N, P, O, and S or each of $R^1$ and $R^2$ may independently be halo, COOR, $CONR_2$, $CF_3$, CN or $NO_2$, wherein R is H or lower alkyl (1-4C) or alkyl (1-6C);

n is 0 or 1;

X is a linker;

with the proviso that Y is not a tropolone, a coumarin, or an antioxidant containing an aromatic group and with the further proviso that if $l^3$ is 0, and either $l^1$ and $l^2$ is 0 or 1 and if $R^1$ and/or R2 represent F in the para position, and Z is N or C where on Y is H or OH, X cannot be —$CH_2CH_2CH_2$—.

The invention is directed to methods to antagonize calcium channel activity using the compounds of formula (1) and thus to treat associated conditions. It will be noted that the conditions may be associated with abnormal calcium channel activity, or the subject may have normal calcium channel function which nevertheless results in an undesirable physical or metabolic state. In another aspect, the invention is directed to pharmaceutical compositions containing these compounds.

The invention is also directed to combinatorial libraries containing the compounds of formula (1) and to methods to screen these libraries for members containing particularly potent calcium channel blocking activity or for members that antagonize other receptors. The libraries may also contain compounds of formula (1) where the provisos do not apply.

BRIEF DESCRIPTION OF THE DRAWINGS

FIGS. 2A-2M show the structures of polylpiperazine-HCl, trifluoromethylphenothiazine; morpholineacetophenone; morpholinebenzophenone; procaine; piperine; fornocaine; flecainide; prenylamine; pridinol; primidone; and piperidolate, respectively.

MODES OF CARRYING OUT THE INVENTION

Figure 1A:
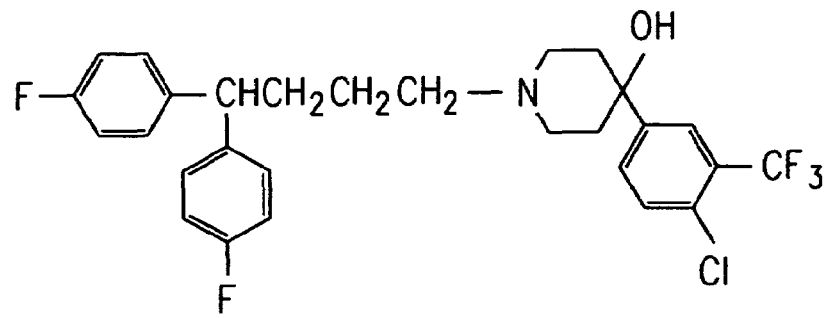
FIGS. 1A-1D show the structures of penfluoridol, pimozide, haloperidol, and flunarizine, respectively.

The compounds of formula (1), useful in the methods of the invention, exert their desirable effects through their ability to antagonize the activity of calcium channels. While the compounds of formula (1) generally have this activity, the availability of a multiplicity of calcium channel blockers permits a nuanced selection of compounds for particular disorders. Thus, the availability of this class of compounds provides not only a genus of general utility in indications that are affected by excessive calcium channel activity, but also provides a large number of compounds which can be mined and manipulated for specific interaction with particular forms of calcium channels. The availability of recombinantly produced calcium channels of the $\alpha_{1A}$-$\alpha_{1E}$, $\alpha_{1G}$ and $\alpha_{1S}$ types set forth above, facilitates this selection process. Dubel, S. J., et al., Proc Natl Acad Sci USA (1992) 89:5058-5062; Fujita, Y., et al., Neuron (1993) 10:585-598; Mikami, A., et al., Nature (1989) 340:230-233; Mori, Y., et al., Nature (1991) 350:398-402; Snutch, T. P., et al., Neuron (1991) 7:45-57; Soong, T. W., et al., Science (1993) 260:1133-1136; Tomlinson, W. J., et al., Neuropharmacology (1993) 32:1117-1126; Williams, M. E., et al., Neuron (1992) 8:71-84; Williams, M. E., et al., Science (1992) 257:389-395; Perez-Reyes, et al. Nature (1998) 391:896-900.

Thus, while it is known that calcium channel activity is involved in a multiplicity of disorders, the types of channels associated with particular conditions is the subject of ongoing data collection. The association of, for example, N-type channels, as opposed to other types, in a specific condition would indicate that compounds of the invention which specifically target N-type receptors are most useful in this condition. Many of the members of the genus of compounds of formula (1) are likely to specifically target N-type channels. Other members of the genus may target other channels.

Among the conditions associated in which blocking excessive calcium would be of therapeutic value are stroke, epilepsy, and chronic and acute pain. Other cardiovascular conditions include hypertension and cardiac arrhythmias. Calcium is also implicated in other neurological disorders such as migraine, epilepsy and certain degenerative disorders.

The availability of the libraries containing the compounds of formula (1) (including those to which the provisos do not apply) also provides a source of compounds which may be screened for activity with regard to additional ion channels and receptors. These channels and receptors are also associated with conditions that are susceptible to treatment. Blockers of sodium channels, for example, are useful as local anesthetics, and in treating cardiac arrhythmias, as anticonvulsants, and in treating hyperkalemic periodic paralysis. Potassium channel blockers are useful in treating hypertension and cardiac arrhythmias; various other receptors are associated with psychoses, schizophrenia, depression, and apnea. Thus, the library of compounds of the invention is useful in standard screening techniques as a source of effective pharmaceutical compounds.

The compounds of formula (1) are defined as shown in terms of the embodiments of their various substituents:

Z may be O, N or C where m has the appropriate value, i.e., O when m is 0, N when m is 1 or C when m is 2. When m is 2, one of the Y substituents is preferably H, OR, $NR_2$, wherein R is H alkyl (1-6C) or one Y may be itself alkyl (1-6C). Preferred forms of Z are N, and C where one Y is H or OH.

Y is H, OH or $NH_2$, or an organic moiety of 1-16C, optionally additionally containing 1-8 heteroatoms selected from the group consisting of N, P, O, S and halo. Preferred forms of at least one Y include those that comprise an aromatic ring system, including fused ring systems and rings containing one or more heteroatoms. Particularly preferred forms of at least one Y are those which include phenyl moieties. The aromatic moieties included within Y may be substituted or unsubstituted; the "substituents" may include alkyl (1-6C), halo, OR, SR, $NR_2$, COOR, or $CONR_2$ wherein each R is independently H or alkyl (1-6C), CN, $CF_3$, or $NO_2$. This set of moieties will be referred to herein as "substituents." Of course, if Z is O, Y is not present (m=0).

Additional preferred embodiments of Y include: aminoindane, azulene, cyclohexane, cyclohexanol, hexahydroazepin, indane, indene, indazole, indole, indolazine, morpholine, phenothiazine, phenoxazine, piperidine, pyrrole, pyridine, pyrimidine, thionaphthene, thiomorpholine, thiazine, and thiazole. When m is 2, the two Y groups may be the same or different and preferred forms are those set forth above. Particularly preferred, however, are embodiments where, when m is 2 and Z is C, one Y is selected from the foregoing list and the other Y is H or OH.

$R^3$ may be alkyl (1-6C), aryl (6-10C), or arylalkyl (7-16C) optionally containing 1-4 heteroatoms selected from the group consisting of N, P, O, S, and halo; preferred embodiments of $R^3$ include methyl. Typically, $l^3$ is 0 or 1.

As n may be 0 or 1, X may be present or not. X is a suitable linker containing 1-10C which may be saturated or unsaturated and may contain a ring. The linker may also contain one or two heteroatoms selected from N, O and S and may be substituted with the "substituents" listed above. Preferred embodiments of X include —$(CH_2)_n$— wherein n is 1-10, preferably 1-6, and more preferably 1-4 or 1-2.

$R^1$ and $R^2$ may independently be alkyl (1-6C), aryl (6-10C), or arylalkyl (7-16C) optionally containing 1-4 heteroatoms and optionally containing any of the "substituents" set forth above or $R^1$ and $R^2$ may themselves independently be said substituents; $l^1$ and $l^2$ are each independently 0-5, but preferably 0-3. Preferred embodiments of $l^1$ and $l^2$ include 1, where the substituent is in the para position (1p) or 3 where the substituents are in the two ortho positions and the para position (3o,p) or 2 where the substituents are in the meta positions (2m). Preferred forms of $R^{21}$ and $R^2$ include phenyl, phenylalkyl, halo, $CF_3$, amino and alkyl.

In the methods of treatment using the compounds of formula (1), Y must be other than a tropolone, a coumarin, or an oxidant containing an aromatic group. In addition, in these methods the compounds of formula (1) cannot include those wherein all of the following are true: $l^3$ is 0; either $l^1$ and $l^2$ are 0 or they are 1 wherein $R^1$ and $R^2$ represent F in the para position; Z is N, or Z is C where one Y is H or OH, and X is —$CH_2CH_2CH_2$—. In the libraries containing compounds of formula (1), these provisos do not apply.

The invention compounds may also be supplied as pharmaceutically acceptable salts. Pharmaceutically acceptable salts include the acid addition salts which can be formed from inorganic acids such as hydrochloric, sulfuric, and phosphoric acid or from organic acids such as acetic, propionic, glutamic, glutaric, as well as acid ion-exchange resins.

Utility and Administration

For use as treatment of animal subjects, the compounds of the invention can be formulated as pharmaceutical or veterinary compositions. Depending on the subject to be treated, the mode of administration, and the type of treatment desired—e.g., prevention, prophylaxis, therapy; the compounds are formulated in ways consonant with these parameters. A summary of such techniques is found in *Remington's Pharmaceutical Sciences*, latest edition, Mack Publishing Co., Easton, PA.

In general, for use in treatment, the compounds of formula (1) may be used alone, as mixtures of two or more compounds of formula (1) or in combination with other pharmaceuticals. Depending on the mode of administration, the compounds will be formulated into suitable compositions to permit facile delivery.

Formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. The formulation will generally include a diluent as well as, in some cases, adjuvants, buffers, preservatives and the like. The compounds can be administered also in liposomal compositions or as microemulsions.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth.

Various sustained release systems for drugs have also been devised. See, for example, U.S. Pat. No. 5,624,677.

Systemic administration may also include relatively non-invasive methods such as the use of suppositories, transdermal patches, transmucosal delivery and intranasal administration. Oral administration is also suitable for compounds of the invention. Suitable forms include syrups, capsules, tablets, as is understood in the art.

For administration to animal or human subjects, the dosage of the compounds of the invention is typically 0.1-100 µg/kg. However, dosage levels are highly dependent on the nature of the condition, the condition of the patient, the judgment of the practitioner, and the frequency and mode of administration.

Screening Methods

The compounds of the invention can be synthesized individually using methods known in the art per se, or as members of a combinatorial library. In general, the benzhydril portion of the molecule, typically containing any $R^1$ and $R^2$ substituents is coupled, along with any linking moiety, to the nitrogen of the morpholine, piperazine or piperidine ring. This ring itself is generally appropriately substituted prior to this coupling. Typically, the benzhydril-linker portion is supplied containing a suitable electron-withdrawing leaving group, thus effecting the coupling to the ring nitrogen.

In addition to condensing a halogenated derivative of a benzhydril moiety to the nitrogen-containing heterocycle, additional conventional ways of condensing the relevant portions of the molecule can be used. For example, a brominated form of appropriately substituted benzhydril may be converted to a Grignard reagent which can then be condensed with, for example, the morpholine, piperidine, or piperazine ring extended at the nitrogen through the moiety $(CH_2)_n$CHO wherein n is an integer from 1-4. Alternatively, a bromoalkylated form of the nitrogen-containing heterocycle may be converted to a Grignard reagent and condensed with the appropriately substituted diphenylketone. In addition, an aminoalkylated form of the nitrogen-containing heterocycle may be condensed with appropriately substituted diphenylketone to obtain the imine which can then be reduced, if desired. Finally, the two phenyl moieties associated with the benzhydril group can be prepared separately and condensed to obtain benzhydril alcohol using a Grignard reagent prepared from one phenyl group and the appropriately substituted benzaldehyde. The benzhydril alcohol can then be brominated or further extended by alkylation and condensed with the morpholine, piperidine or piperazine derivative.

Synthesis of combinatorial libraries is now commonplace in the art. Suitable descriptions of such syntheses are found, for example, in Wentworth, Jr., P., et al., *Current Opinion in Biol* (1993) 9:109-115; Salemme, F. R., et al., *Structure* (1997) 5:319-324. The libraries contain compounds with various embodiments of $R^1$, $R^2$, $R^3$, X, Y and Z. These libraries, which contain, as few as 10, but typically several hundred members to several thousand members, may then be screened for compounds which are particularly effective against a specific subtype of calcium channel. In addition, using standard screening protocols, the libraries may be screened for compounds which block additional channels or receptors such as sodium channels, potassium channels and the like.

Methods of performing these screening functions are well known in the art. Typically, the receptor to be targeted is expressed at the surface of a recombinant host cell such as human embryonic kidney cells. The ability of the members of the library to bind the receptor or channel is measured, for example, by the ability of the compound in the library to displace a labeled binding ligand such as the ligand normally associated with the receptor or an antibody to the receptor. More typically, ability to antagonize the receptor is measured in the presence of the appropriate agonist and the ability of the compound to interfere with the signal generated is measured using standard techniques.

In more detail, one method involves the binding of radiolabeled agents that interact with the calcium channel and subsequent analysis of equilibrium binding measurements including, but not limited to, on rates, off rates, $K_d$ values and competitive binding by other molecules. Another method involves the screening for the effects of compounds by electrophysiological assay whereby individual cells are impaled with a microelectrode and currents through the calcium channel are recorded before and after application of the compound of interest. Another method, high-throughput spectrophotometric assay, utilizes loading of the cell lines with a fluorescent dye sensitive to intracellular calcium concentration and subsequent examination of the effects of compounds on the ability of depolarization by potassium chloride or other means to alter intracellular calcium levels.

The following examples are intended to illustrate but not to limit the invention.

EXAMPLE 1

Correlation of Calcium Channel Blocking with the Presence of a Piperidine/Piperazine Ring Antagonist activity was measured using nystatin patch recordings on human embryonic kidney cells either stably or transiently expressing $\alpha_{1B}+\alpha_{2b}+\beta_{1b}$ channels with 5 mM barium as a charge carrier.

For transient expression, host cells, such as human embryonic kidney cells, HEK 293 (ATCC# CRL 1573) are grown in standard DMEM medium supplemented with 2 mM glutamine and 10% fetal bovine serum. HEK 293 cells are transfected by a standard calcium-phosphate-DNA coprecipitation method using the $\alpha_{1B}+\beta_{1b}+\alpha_{2}\delta$ N-type calcium channel subunits in a vertebrate expression vector (for example, see *Current Protocols in Molecular Biology*).

After an incubation period of from 24 to 72 hrs the culture medium is removed and replaced with external recording solution (see below). Whole cell patch clamp experiments are performed using an Axopatch 200B amplifier (Axon Instruments, Burlingame, Calif.) linked to an IBM compatible personal computer equipped with pCLAMP software. The external recording solution is 20 mM $BaCl_2$, 1 mM $MgCl_2$, 10 mM HEPES, 40 mM TEACl, 10 mM Glucose, 65 mM CsCl (pH 7.2). The internal pipette solution is 105 mM CsCl, 25 mM TEACl, 1 mM $CaCl_2$, 11 mM EGTA, 10 mM HEPES (pH 7.2). Currents are typically elicited from a holding potential of −100 mV to various test potentials. Data are filtered at 1 kHz and recorded directly on the hard drive of a personal computer. Leak subtraction is carried out on-line using a standard P/5 protocol. Currents are analyzed using pCLAMP versions 5.5 and 6.0. Macroscopic current-voltage relations are fitted with the equation $I=\{1/(1+\exp(-(V_m-V_h)/S)\}\times G-(V_{m-Erev})$, where $V_m$ is the test potential, $V_h$ is the voltage at which half of the channels are activated, and S reflects the steepness of the activation curve and is an indication of the effective gating charge movement. Inactivation curves are normalized to 1 and fitted with $I=(1/1+\exp((V_m-V_h)/S)$ with $V_m$ being the holding potential.

Figure 1B:
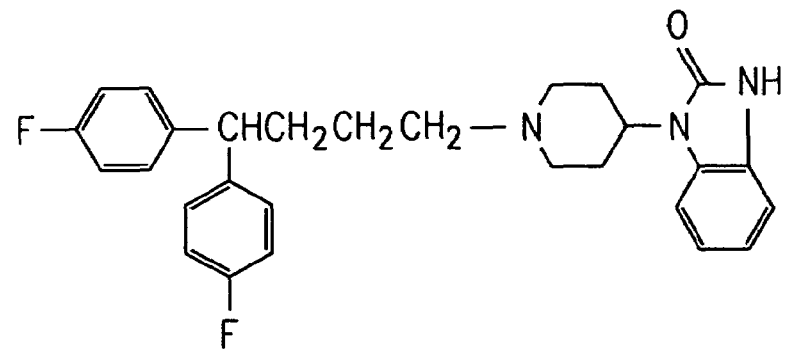
Figure 1C:
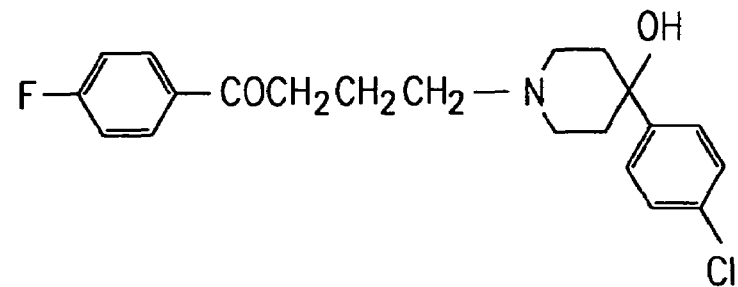
Figure 1D:
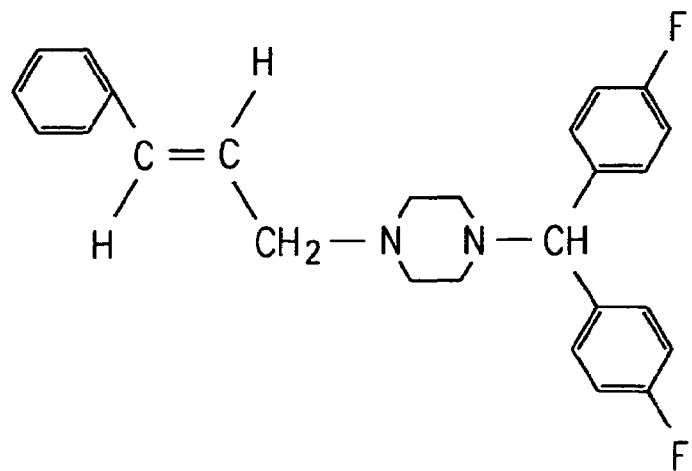
Figure 2A:
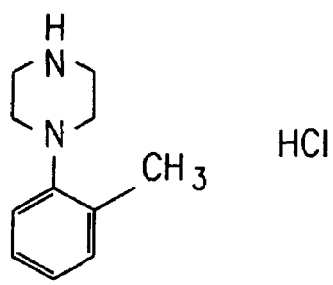
Figure 2B:
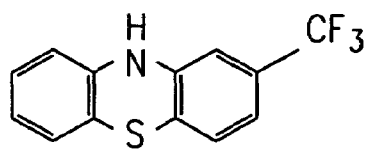
Figure 2C:
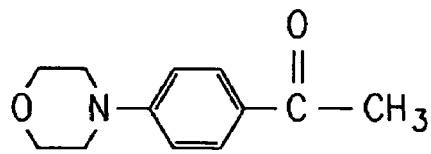
Figure 2D:
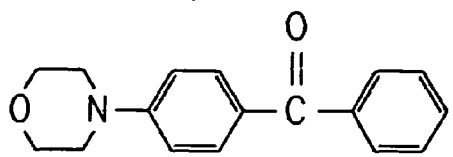
Figure 2E:
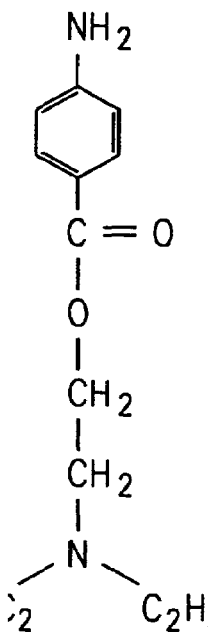
Figure 2F:
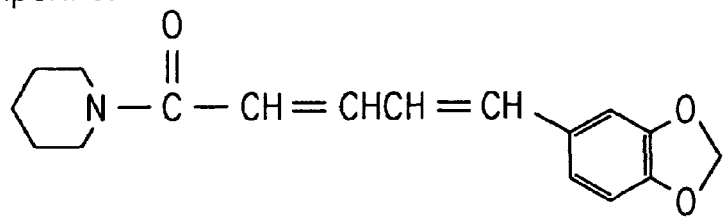
Figure 2G:
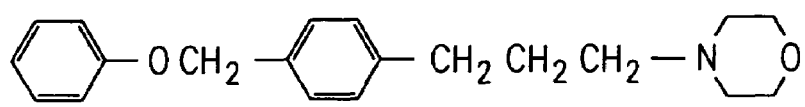
Figure 2H:
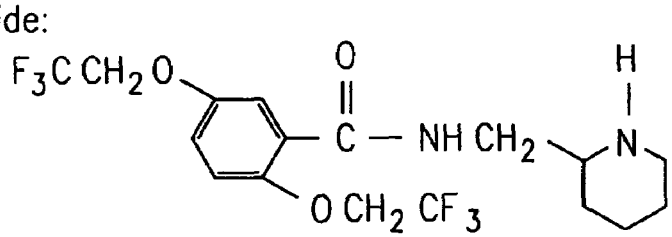
Figure 2J:
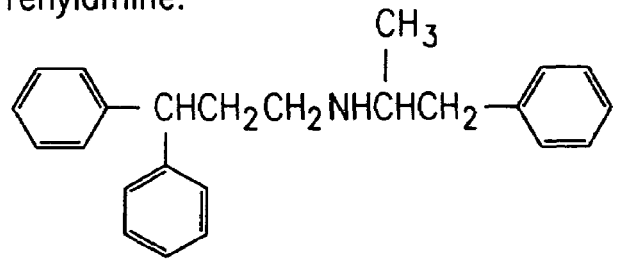
Figure 2K:
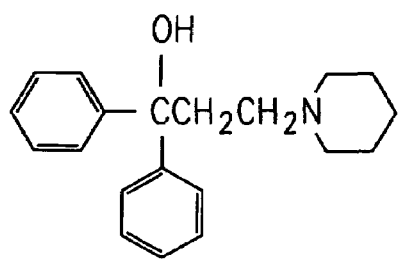
Figure 2L:
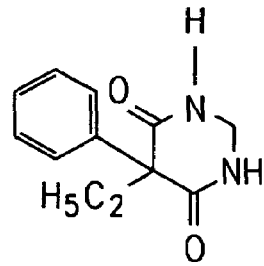
Figure 2M:
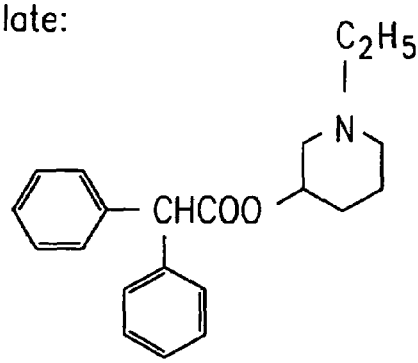

The results of three experiments were averaged. The structures of most of the compounds tested are shown in FIGS. 1 and 2. The compounds of FIG. 1 showed effective blocking activity:

Penfluridol has an $IC_{50}$ of 5 µM; the block develops over 60-90 sec at 10 µM concentrations and is poorly reversible (pKa=9.0).

Pimozide shows an $IC_{50}$ of about 2-3 µM; the block develops in 90 sec at 10 µM and is completely reversible (pKa=7.32). More than 80% of the activity is blocked at 10 µM.

Haloperidol has an $IC_{50}$ of 90 µM and the block develops in less than 16 sec. It is reversible within 15 sec (pKa=8.3). At 10 µM concentrations, the block is about 10%.

Flunarizine has an $IC_{50}$ of <1 µM; the block develops over about 120 sec at 10 µM concentration and reverses over about 5 min. The block is 90-95% effective at 10 µM.

On the other hand, less activity was shown by prenylamine ($IC_{50}$>40 µM); pridinol ($IC_{50}$>400 µM); primidone ($IC_{50}$>500 µM); and piperidolate ($IC_{50}$>300 µM). Additional compounds which showed high values for $IC_{50}$ include bupivacaine, tolylpiperazine, piperine, trifluoromethylphenothiazine, morpholineacetophenone, morpholinebenzophenone and chloroethylpiperazine. As shown, the compounds of formula (1) which show activity comprise those wherein X contains two phenyl rings and Y contains one phenyl ring, optionally substituted by halo.

EXAMPLE 2

Synthesis of Compounds of Formula (1)

Following the general procedure described above, the following compounds of formula (1) are synthesized as shown in Table 1.

TABLE 1

| $R^1$ | $L^1$ | $R^2$ | $l^2$ | X | n | Y | Y | $R^3$ | $l^3$ | Z | m |
|---|---|---|---|---|---|---|---|---|---|---|---|
| $CH_3$ | 1p | $CH_3$ | 1p | — | 0 | Φ | — | — | 0 | N | 1 |
| — | 0 | Cl | 2m | —$CH_2$— | 1 | —$CH_2\phi$ | H | $CH_3$ | 1 | CH | 2 |
| F | 1p | F | 3o,p | —$CH_2CH_2$— | 1 | —$CH_2CH\phi$ | OH | $CH_3$ | 1 | COH | 2 |

TABLE 1-continued

| R¹ | L¹ | R² | l² | X | n | Y | Y | R³ | l³ | Z | m |
|---|---|---|---|---|---|---|---|---|---|---|---|
| — | 0 | CF₃ | 1p | — | 0 | [pyrrolidinone-indole structure] | H | C₂H₅ | 1 | CH | 2 |
| Φ | 1p | — | 0 | —(CH₂)₃— | 1 | Amino-indane | — | — | 0 | O | — |
| CH₃ | 3o,p | COOMe | 2m | —CH₂— | 1 | Azulene | Azulene | C₂H₅ | 1 | C | 2 |
| Cl | 3o,p | Cl | 2m | —CONH— | 1 | Cyclohexane | — | CH₃ | 1 | N | 1 |
| CN | 2m | CF₃ | 2m | —CH=CH— | 1 | Pyrimidine | — | — | 0 | N | 1 |
| N(CH₃)₂ | 1p | C₂H₅ | 2m | —CH₂CH₂— | 1 | Indole | Pyrrole | — | 0 | C | 2 |

The invention claimed is

1. A method to treat pain in a subject which method comprises administering to a subject in need of such treatment a compound of the formula

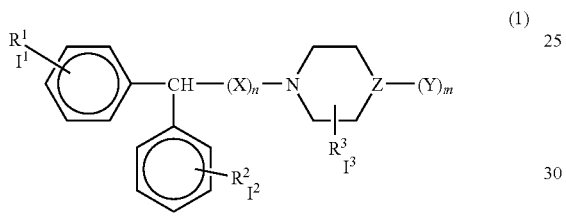

(1)

wherein m is 0, 1 or 2;
wherein when m is 0, Z is O, when m is 1, Z is N, and when m is 2, Z is C;
Y is H, OH, NH₂, or an organic moiety of 1-20C, optionally additionally containing 1-8 heteroatoms selected from the group consisting of N, P, O, S and halo;
each $l^1$ and $l^2$ is independently 0-5;
$l^3$ is 0 or 1;
each of R¹, R² and R³ is independently alkyl (1-6C), aryl (6-10C) or arylalkyl (7-16C) optionally containing 1-4 heteroatoms selected from the group consisting of halo, N, P, O, and S or each of R¹ and R² may independently be halo, COOR, CONR₂, CF₃, CN or NO₂, wherein R is H or lower alkyl (1-4C) or alkyl (1-6C);
n is 0 or 1;
X is a linker;
with the proviso that Y is not a tropolone, a coumarin, or an antioxidant containing an aromatic group and with the further proviso that if $l^3$ is 0, and either $l^1$ and $l^2$ is 0 or 1 and if R¹ and/or R² represent F in the para position, Z cannot be N or C.

2. A pharmaceutical composition for use in treating pain which composition comprises, in admixture with a pharmaceutically acceptable excipient, a dosage amount of a compound of the formula

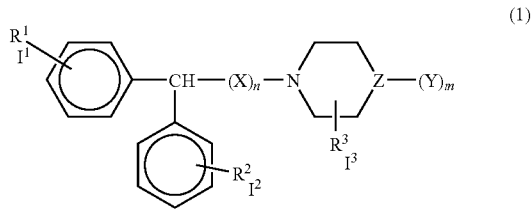

(1)

wherein m is 0, 1 or 2;
wherein when m is 0, Z is O, when m is 1, Z is N, and when m is 2, Z is C;
Y is H, OH, NH₂, or an organic moiety of 1-20C, optionally additionally containing 1-8 heteroatoms selected from the group consisting of N, P, O, S and halo;
each $l^1$ and $l^2$ is independently 0-5;
$l^3$ is 0 or 1;
each of R¹, R² and R³ is independently alkyl (1-6C), aryl (6-10C) or arylalkyl (7-16C) optionally containing 1-4 heteroatoms selected from the group consisting of halo, N, P, O, and S or each of R¹ and R² may independently be halo, COOR, CONR₂, CF₃, CN or NO₂, wherein R is H or lower alkyl (1-4C) or alkyl (1-6C);
n is 0 or 1;
X is a linker;
with the proviso that Y is not a tropolone, a coumarin, or an antioxidant containing an aromatic group and with the further proviso that if $l^3$ is 0, and either $l^1$ and $l^2$ is 0 or 1 and if R¹ and/or R² represent F in the para position, and Z cannot be N or C.

* * * * *

UNITED STATES PATENT AND TRADEMARK OFFICE
CERTIFICATE OF CORRECTION

PATENT NO. : 7,666,865 B2  Page 1 of 1
APPLICATION NO. : 11/601005
DATED : February 23, 2010
INVENTOR(S) : Snutch et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 650 days.

Signed and Sealed this

Seventh Day of December, 2010

David J. Kappos
*Director of the United States Patent and Trademark Office*